United States Patent [19]

Jackson

[11] Patent Number: 4,619,947
[45] Date of Patent: Oct. 28, 1986

[54] CHEMICAL PROCESS

[75] Inventor: Samuel D. Jackson, Runcorn, England

[73] Assignee: Imperial Chemical Industries PLC, London, England

[21] Appl. No.: 756,089

[22] Filed: Jul. 17, 1985

[30] Foreign Application Priority Data

Aug. 8, 1984 [GB] United Kingdom ............... 8420149

[51] Int. Cl.[4] .......................... C07C 1/04; C07C 27/06
[52] U.S. Cl. .................................... 518/716; 518/709; 518/715; 518/719; 518/721; 518/728
[58] Field of Search ............... 518/715, 716, 719, 721, 518/728, 709

[56] References Cited

U.S. PATENT DOCUMENTS 4,207,208 6/1980 Lucki et al. ..................... 518/709
4,260,518 4/1981 Katzer et al. ................... 518/709

*Primary Examiner*—Howard T. Mars
*Attorney, Agent, or Firm*—Cushman, Darby & Cushman

[57] ABSTRACT

A method for the preparation of hydrocarbons and oxygenated hydrocarbons which comprises contacting a gaseous mixture of carbon monoxide, hydrogen and oxygen with a catalyst comprising a metal of Group VII or Group VIII of the Periodic Table, the amount of oxygen not exceeding 10% by volume based on the volume of hydrogen.

4 Claims, No Drawings

CHEMICAL PROCESS

This invention relates to a chemical process and more particularly to a process for the production of useful organic materials from synthesis gas.

Processes for the catalytic conversion of synthesis gas (a mixture of carbon monoxide and hydrogen) to useful organic materials are well known and are used industrially, for example in the manufacture of methanol. The products obtained from these processes vary according to the particular catalyst and reaction conditions employed and can include both hydrocarbons and oxygenated hydrocarbons.

Many variations in the conditions employed have been proposed, the usual objects being to improve the overall conversion of synthesis gas to useful materials and/or to increase selectively the production of one or more products of particular value, for example alcohols. These variations usually include changes in the composition or form of the catalyst or its support and/or changes in the temperature/pressure conditions.

It has now been found that, when a Group VII or Group VIII metal is used as catalyst, increased conversion rates and/or improvements in selectivity towards particular products may be obtained by including a minor proportion of oxygen with the synthesis gas to be converted.

Accordingly, the invention provides a method for the preparation of hydrocarbons and oxygenated hydrocarbons which comprises contacting a gaseous mixture of carbon monoxide, hydrogen and oxygen with a catalyst comprising a metal of Group VII or Group VIII of the Periodic Table, the amount of oxygen not exceeding 10% by volume based on the volume of hydrogen.

The conditions of the reaction performed in accordance with the method of the invention are generally conventional for synthesis gas conversions with respect to temperature, pressure, catalysis and gas composition with the additional feature of the inclusion of oxygen in the gas feed.

Thus, whilst the molar ratio of carbon monoxide to hydrogen in the gas feed may vary widely, it is normally in the range 10:1 to 1:10, preferably 3:1 to 1:3. The amount of oxygen is preferably within the range from 0.01% to 1.0% of the hydrogen on a molar basis. Inert diluents such as nitrogen, argon or helium may also be present in the feed.

The reaction temperature is suitably in the range 50° to 500° C., preferably 85° to 400° C. with pressures of up to 250 bars, preferably in the range 5 to 150 bars. The gas hourly space velocity (volume of synthesis gas, at STP, per volume of catalyst per hour) is suitably in the range from 250 to $10^5$ per hour, preferably from 600 to 25000 per hour.

The Group VII or Group VIII metal catalyst may be carried on a conventional support. Rhenium is an effective Group VII metal whilst in Group VIII, rhodium and the other platinum group metals are preferred. The catalyst may be prepared by depositing the metallic component on the support material by impregnation, precipitation or any of the other known techniques for catalyst preparation, the support material then being dried and calcined, the latter preferably under reducing conditions. Mixtures of Group VII and/or Group VIII metals may be used.

Suitable support materials include silica, alumina, silica/alumina, zeolites, magnesia, thoria, titania, chromia, zirconia, tungsten oxide, molybdenum oxide and active carbon. Suitably, the support has a relatively high surface area, for example from 1 to 300 square meters per gram. The amount of catalyst present on the support is suitably from 0.1 to 20 weight percent, preferably from 0.5 to 10 weight percent, of metal based on the combined weight of the metal and the support. The catalyst may be employed in the form of a fixed or fluidised bed of appropriate size.

Although the method of the invention may be carried out in a batchwise manner, it is preferably carried out continuously. Conventional means may be used to recover the reaction product and to separate the various constituents thereof.

In many cases it can be shown that the presence of oxygen in the synthesis gas feed results in an increased conversion rate to useful products. An improvement in the selectivity towards oxygenated hydrocarbons at the expense of the less useful hydrocarbons can also be demonstrated. The oxygenated hydrocarbons particularly include those having two or more carbon atoms, for example alcohols such as ethanol. Furthermore, catalysts that have been deactivated by synthesis gas can be rapidly and efficiently re-activated by a synthesis gas stream containing a minor proportion of oxygen.

The invention is illustrated but not limited by the following Examples.

EXAMPLE 1

A carbon monoxide/hydrogen stream (1:2 molar) was passed over a rhodium on magnesium stannate catalyst at 300° C., a pressure of 10 bars and a GHSV of 1200. The observed activity was 0.028 moles kg catalyst$^{-1h}$.

When 0.1% by volume of oxygen ws included in the gas feed, the activity increased by 16.4% to 0.0326 moles kg catalyst$^{-1}$h$^{-1}$.

EXAMPLE 2

The procedure of Example 1 was repeated using a rhodium on alumina catalyst at 250° C. Inclusion of 0.2% by volume of oxygen in the synthesis gas increased the total activity from 0.4438 to 0.4894 moles kg catalyst $^{-1}$h$^{-1}$.

EXAMPLE 3

A carbon monoxide/hydrogen stream (1:2 molar) was passed over a sodium-palladium catalyst supported on oxalic acid washed silica at 325° C., a pressure of 10 bars and a GHSV of 1200. The hydrocarbons/oxygenated hydrocarbons ratio of the products obtained was 0.875.

When 0.16% by volume of oxygen was included in the gas feed, the ratio fell to 0.25.

EXAMPLE 4

The procedure of Example 3 was repeated using a rhodium catalyst supported on oxalic acid washed silica at 225° C. Inclusion of 0.18% by volume of oxygen in the synthesis gas reduced the hydrocarbons/oxygenated hydrocarbons ratio from 11.5 to 5.7.

EXAMPLE 5

Rhodium (III) chloride (0.407 g) was dissolved in distilled water and the resulting solution was added to tungsten trioxide (10 g) to give a suspension which was then evaporated to dryness under a stream of nitrogen at 25° C. The dried catalyst precursor was reduced by being heated to 300° C. in a nitrogen/hydrogen stream (4:1 molar) and held at that temperature for 0.25 h. The resulting catalyst, containing 2% by weight of rhodium based on the weight of tungsten oxide, was then cooled under the nitrogen/hydrogen stream to the desired reaction temperature and the gas flow changed to carbon monoxide/hydrogen (1:2 molar) at a pressure of 10 bars and a GHSV of 1200.

The activity of this catalyst at 150° C. was 0.0465 moles kg catalyst $^{-1}h^{-1}$ in the steady state. After deactivation, the activity under the same conditions was 0.0017 moles kg catalyst $^{-1}h^{-1}$. On introducing 0.1% by volume of oxygen into the feed stream, an activity of 0.0535 moles kg catalyst $^{-1}h^{-1}$ was immediately obtained.

EXAMPLE 6

A ruthenium on tungsten trioxide catalyst was prepared in a manner similar to that for the catalyst of Example 5. When a carbon monoxide/hydrogen (1:2 molar) gas stream was passed over this catalyst, at 150° C., 10 bars pressure and a GHSV of 1200, the total selectivity to oxygenated products was 4.9%; when 0.05% by volume oxygen was added to the synthesis gas, the oxygenate selectivity increased to 21.9%.

EXAMPLE 7

A carbon monoxide/hydrogen stream (1:2 molar) was passed over an iron on oxalic acid washed silica catalyst at 250° C., a pressure of 10 bars and a GHSV of 1200. The observed hydrocarbon/oxygenated hydrocarbons ratio was 5.4. When 0.05% by volume oxygen was added to the feedstream, this ratio fell to 3.3.

EXAMPLE 8

When carbon monoxide/hydrogen (1:2 molar) was passed over a ruthenium on tungsten trioxide catalyst at 150° C., a pressure of 10 bars and a GHSV of 1200, no acetaldehyde or methyl acetate were formed. On addition of 0.05% by volume oxygen to the feedstream, both acetaldehyde and methyl acetate were formed at rates of 0.0014 and 0.0022 moles kg catalyst $^{-1}h^{-1}$ respectively.

I claim:

1. A method for the preparation of hydrocarbons and oxygenated hydrocarbons which comprises contacting a gaseous mixture of carbon monoxide, hydrogen and oxygen with a catalyst comprising a metal of Group VII or Group VIII of the Periodic Table, the amount of oxygen not exceeding 10% by volume based on the volume of hydrogen.

2. A method according to claim 1 wherein the amount of oxygen is within the range from 0.01% to 1.0% of the hydrogen on a molar basis.

3. A method according to claim 1 wherein the Group VIII metal is a platinum group metal.

4. A method according to claim 3 wherein the platinum group metal is rhodium.

* * * * *